United States Patent [19]
Klecker

[11] 3,974,533
[45] Aug. 17, 1976

[54] DISPOSABLE ENEMA EVACUANT COLLECTION SYSTEM

[76] Inventor: James D. Klecker, 1879 Fairmount Ave., St. Paul, Minn. 55105

[22] Filed: Oct. 3, 1974

[21] Appl. No.: 511,783

[52] U.S. Cl. .................................. 4/112; 128/283; 128/295
[51] Int. Cl.² ........................................ A47K 11/06
[58] Field of Search .............. 4/110, 112, 113, 120; 128/283, 295, DIG. 24; 5/90

[56] References Cited
UNITED STATES PATENTS

| | | | |
|---|---|---|---|
| 1,468,603 | 9/1923 | Mack | 4/112 |
| 2,724,122 | 11/1955 | Tennyson | 4/113 |
| 3,187,750 | 6/1965 | Tenczar, Jr. | 128/DIG. 24 |
| 3,703,731 | 11/1972 | Leiser | 4/110 |

Primary Examiner—Richard E. Aegerter
Assistant Examiner—Stuart S. Levy
Attorney, Agent, or Firm—John W. Adams

[57] ABSTRACT

This is a disposable enema evacuant collection system comprising a bedpan having an interior bottom surface sloping toward a large discharge opening and a transparent plastic multi-compartmented receptacle with a conduit extending therebetween, and having controllable divider branches communicating with the respective compartments of the receptacle and means for selecting the respctive branch into which the evacuant is discharged thereby facilitating respective measurement of the evacuant, providing a more efficient and less demeaning manner of enema administration, and also greatly facilitating the obtaining of a fecal specimen for analysis.

1 Claim, 2 Drawing Figures

U.S. Patent    Aug. 17, 1976    3,974,533
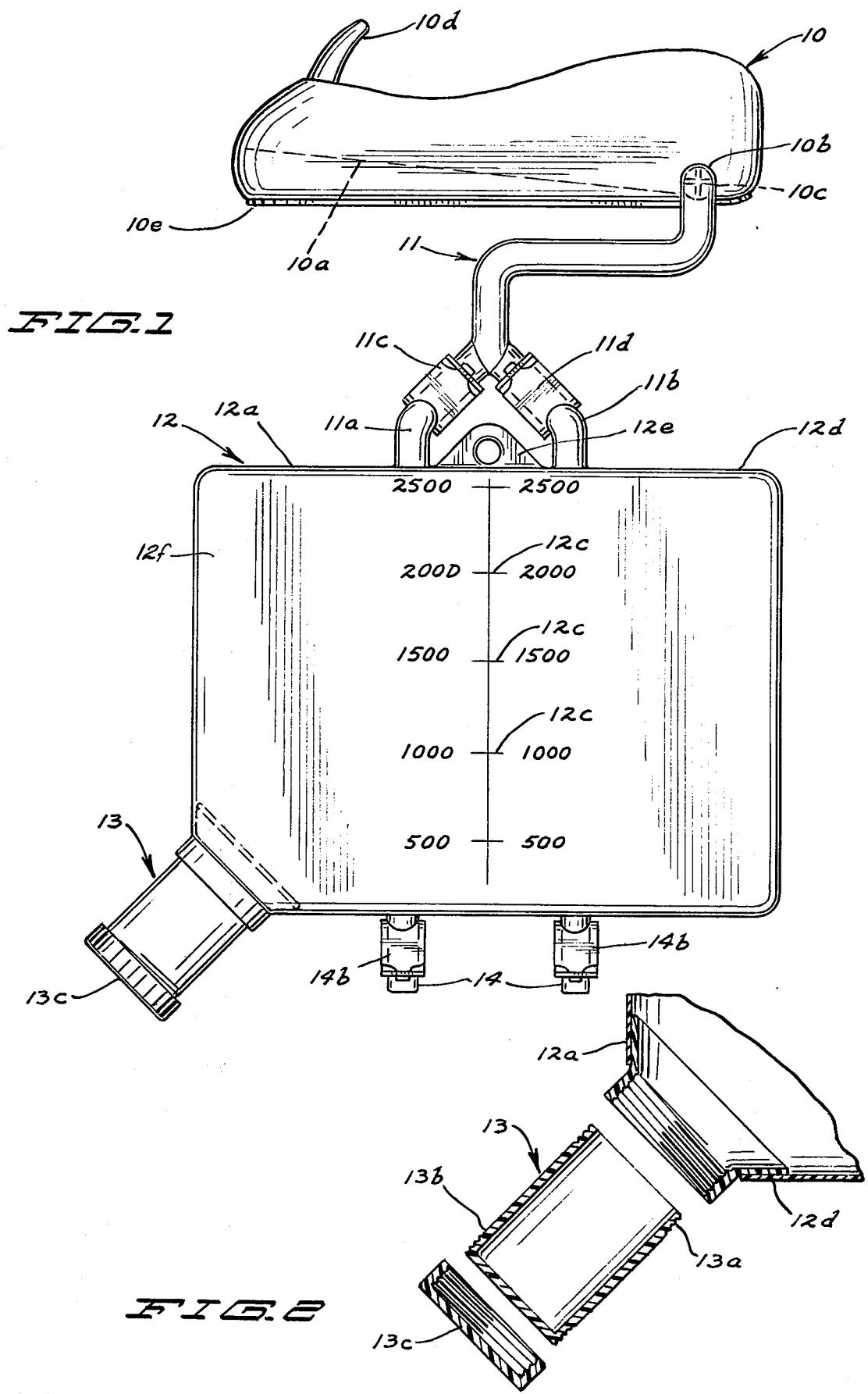

DISPOSABLE ENEMA EVACUANT COLLECTION SYSTEM

At present enema administration it is best a demeaning, inefficient and unprofessional medical procedure. It requires extensive moving of the patient and the physical labor of at least three medical personnel to accomplish it. The existing method is often personally embarrassing to the patient and equally distasteful to the medical personnel involved. Enema administration on a bedridden patient frequently produces spillage on the bed clothes, the surrounding hospital area and on the patient himself. In addition to the personal and efficiency difficulties, there is a distinct problem in the medical determination of enema evacuant, and the administrating personnel has little empirical evidence of the evacuant progress oftentimes causing an unnecessary and prolonged enema procedure. There is also the problem of obtaining representative and undiluted stool specimens as they are now usually secured from the bedpan or toilet and are difficult and messy to get into a container, and also frequently include excessive dilution. This type of specimen lowers the quality needed for accurate laboratory evaluation. In addition, this invention provides a conveniently positioned specimen container removably attached to the discharge opening of one of the compartments.

Therefore, it is an object of this invention to provide a disposable sealed enema evacuant collection system which permits a less demeaning, more efficient, and medically more professional method of enema administration.

It is another object of this invention to prevent extensive and unnecessary movement of the patient and embarrassment and accidental spillage of the evacuant.

It is another object of this invention to provide such a system which includes a bedpan with an interior bottom surface sloping toward a large discharge opening and having a conduit with selectively controllable divider branches respectively connected to the compartments of a multicompartmented receptacle to permit separation of the evacuant of the first enema from the evacuant of subsequent enemas without removing the patient from the bedpan.

It is a further object of this invention to provide a separable specimen-collecting container with closure cap connected to the compartment receiving the initial enema evacuant to facilitate obtaining a representative specimen with a minimum of dilution in a convenient and least distasteful manner.

It is a further object of the invention to provide a enema evacuant collection system that can be used for the several enemas that may be necessary for total cleansing effect, but that is disposable after such use. These and other objects and advantages of this invention will be apparent from the following description made in connection with the accompanying drawing wherein like reference characters refer to similar parts throughout the several views and in which:

FIG. 1 is a schematic view showing the system in operative position;

FIG. 2 is a side elevational view of the bedpan.

As shown in the accompanying drawings, my Disposable Enema Evacuant Collection System includes a bedpan 10, a transparent plastic multi-compartmented receptacle 12 with a conduit 11 connecting the same. The conduit is divided to provide separate branches for each of the compartments of the receptacle 12.

The bedpan 10 has an interior bottom surface 10a sloping toward a large discharge opening 10b near one end thereof and having a grid section 10c to prevent excessively sized fecal material from passing into the conduit 11 and clogging the same. The bedpan 10 also has a removably attached urine deflector 10d and a generally flat exterior bottom surface 10e covered with a high friction material to prevent slippage on the bed covering.

In the form shown the receptacle 12 has a pair of separate compartments respectively designated 12a and 12b though more compartments could be added, if desired. Each compartment has volumetric calibrations 12c and a transparent side wall panel 12f. Each compartment also has separate drain openings 14a and 14b, respectively, to permit drainage of several successive enemas frequently required for total cleansing. The multi-compartment receptacle 12 is suspended by a supporting member 12e on the top of said receptacle.

The conduit 11 is large enough to accomodate the enema evacuant after passing through the grid 10c and is removably attached by any suitable means to the bedpan discharge opening 10b. The conduit 11 includes a pair of divider branches 11a and 11b, respectively, for delivering the enema evacuant to the respective compartments 12a and 12b. These branches 11a and 11b have shut-off means such as clamps 11c and 11d for selecting the particular compartment into which the evacuant is carried enabling the more solid fecal enema evacuant from the first enema to be separated from the diluted evacuant from subsequent enemas. Complete enema discharge is essential and is facilitated by the calibrated compartments and also isolation for test purposes of the first enema evacuant is thus permitted.

There is a removably attached separable specimen-collecting rigid container 13 with threaded exterior portions 13a and 13b, the top and bottom thereof, respectively. The top threaded portion 13a fits into a cooperatively threaded interior portion of a large discharge opening 12d in the bottom of the compartment 12a to provide a convenient specimen container attached directly to the collection system. There is also a removably attached sealing cover 13c attachable to both ends of specimen-collecting container 13 depending on whether it is attached to discharge opening 12d for collection of samples or for transportation to a testing laboratory.

It will be seen that I have provided a simple, yet highly efficient enema collection system which obviates the necessity for repeated removal and dumping of the bedpan while permitting isolation of selected portions of the enema evacuant.

It will, of course, be understood that various changes may be made in the form, details, arrangements and proportions of the parts without departing from the scope of this invention as set forth in the appended claims.

What is claimed is:

1. A disposable enema evacuant collection system comprising a bedpan having
   a large discharge opening, and
   an interior bottom surface sloping toward said opening
   a flexible plastic receptacle and,
   a conduit extending between the discharge opening and the receptacle valve means for controlling the flow through said conduit, a discharge opening in the bottom of said receptacle for dumping the evacuant from said receptacle, said receptacle having a plurality of compartments therein, said conduit having a plurality of branches respectively delivering to said compartments, said valve means including means for selectively controlling flows into the desired branch to control the compartment into which the evacuant is discharged, and each compartment having a separate discharge opening in the bottom thereof, and a separate specimen-collecting rigid container removably attached to the bottom of one of said compartments and closed at one end and open at the other end, a threaded exterior portion on both ends of said container, and a cooperatively threaded interior portion formed at the discharge opening of said compartment for removably attaching said container thereto and a closure cap normally threadably attached at the closed end of said rigid container, but removable therefrom for closure attachment to the open end of the container after removal from the receptacle.

* * * * *